United States Patent
Petrova et al.

(10) Patent No.: US 6,753,392 B1
(45) Date of Patent: Jun. 22, 2004

(54) FUNCTIONAL TRIFLUOROVINYL MONOMERS AND THEIR COPOLYMERISATION WITH FLUORINATED OLEFINS

(75) Inventors: Petya Petrova, Sliven (BG); Bruno Ameduri, Montpellier (FR); Georges Kostov, Bourgas (BG); Bernard Boutevin, Montpellier (FR)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/856,774

(22) PCT Filed: Nov. 22, 1999

(86) PCT No.: PCT/EP99/09147

§ 371 (c)(1),
(2), (4) Date: Jul. 31, 2001

(87) PCT Pub. No.: WO00/31009

PCT Pub. Date: Jun. 2, 2000

(30) Foreign Application Priority Data

Nov. 25, 1998 (FR) .............................................. 98 14931

(51) Int. Cl.$^7$ ............................................. C08F 114/18
(52) U.S. Cl. ...................... 526/243; 526/245; 526/246; 525/276
(58) Field of Search ................................ 526/243, 245, 526/246; 525/276

(56) References Cited

U.S. PATENT DOCUMENTS 3,483,263 A 12/1969 Schlichting ................. 260/633
5,514,717 A 5/1996 Phillion et al. ............. 514/601

FOREIGN PATENT DOCUMENTS

EP 0135917 4/1985
EP 0138091 4/1985
WO 86/07590 12/1986

OTHER PUBLICATIONS

Dubufftet, T., et al, *J. Organometallic Chem* 341:11–18 (1988) (In French).

Nguyen, T., et al, "Primary Polyfluoroallylic Alcohols. Preparation and Isomerization into 2–Fluoroacrylic Acid Fluoride and 1–Fluoro Vinyl Ketones", *J. Org. Chem* 54:5640–5642 (1989).

Su, Debao, et al, "Synthesis of trans–1,2–Difluorethenediyl-bis–(phosphonic acid) and Other Unsaturated Phosphonic Acids, " *J. Am. Chem. Soc.* 112:3152–3155 (1990).

Tada, Yuji, et al, "Ion–conduction of lithium fluoralkyl–sulfonates in oligo(oxyethylene)—branched poly(phospha–zene)," *Makromol. Chem* 194:2163–2171 (1993).

Dolbier Jr., W. R., et al, "Cyclization reactivities of fluorinated hex–5–enyl radicals," *J. Chem. Soc.,Perkin Trans.* 2:219–231 (1998).

Améduri, B., et al, "Synthesis and polymerization of fluorinated monomers bearing a reactive lateral group. Part 3$^1$–Synthesis of trifluorovinyl . . . ," *J. of Fluorine Chem.*92:69–76 (1998).

Améduri, B., et al, "Synthesis and polymerization of fluorinated monomers bearing a reactive lateral group$^1$. Part 4.Preparation of functional perfluorovinyl . . . ," *J.Fluorine Chem.*92:77–84 (1998).

Améduri, A., et al, "Synthesis and polymerization of fluorinated monomers bearing a reactive lateral group. Part 5$^1$–Radical addition of iodine . . . ," *J. of Fluorine Chem* 93:117–127 (1999).

Améduri, B., et al, "Synthesis and polymerization of fluorinated monomers bearing a reactive lateral group. Part 6$^1$–Synthesis of trifluorovinyl epoxide . . . " *J. of Fluorine Chem.*93:139–144 (1999).

*Primary Examiner*—Bernard Lipman
(74) *Attorney, Agent, or Firm*—Connolly Bove Lodge & Hutz LLP

(57) ABSTRACT

Functional trifluorovinyl monomers, process for the copolymerization of trifluorovinyl monomers with fluoroolefins and use of these trifluorovinyl monomers in forming fluoroelastomers.

Copolymers resulting from this copolymerization process and process for crosslinking these copolymers.

6 Claims, No Drawings

FUNCTIONAL TRIFLUOROVINYL MONOMERS AND THEIR COPOLYMERISATION WITH FLUORINATED OLEFINS

The present invention relates to fluoromonomers. It also relates to processes for the copolymerization of fluoromonomers with fluoroolefins, to the resulting copolymers and to the use of these monomers in forming in particular fluoroelastomers. In addition, the present invention relates to a process for the crosslinking of these copolymers.

A large number of fluoromonomers have already been disclosed in the literature.

The synthesis of fluoroolefins corresponding to the general formula $CF_2=CF(CF_2)_m(CH_2)_nOH$ (with m=0 to 10 and n=1 to 4) is disclosed in Patent Application EP 0 138 091. The use of fluoroolefins as comonomers of vinylidene fluoride is also envisaged.

Patent Application EP 0 135 917 discloses fluorocopoymers formed by copolymerization of vinylidene fluoride with fluoroolefins of general formula $CF_2=CF(CF_2)_m(CH_2)_nX$ (with X=OH, COOH or an epoxide group, m=0 to 10 and n=1 to 4). The copolymerization of some of these compounds with vinylidene fluoride is described therein.

Patent U.S. Pat. No. 3,483,263 discloses the synthesis of unsaturated haloalcohols corresponding to the formula $CX_1X_2=CX_3—A—OH$ in which $X_1$ to $X_3$ represent halogen atoms and A represents an alkylene group comprising at least two carbon atoms.

T. Nguyen et al., in J. Organic. Chem., 54(23), 5640–5642, 1989, disclose the synthesis of a compound corresponding to the formula $CF_2=CFCH_2OH$ by addition of methyllithium to 2,2,3,3-tetrafluoropropanol.

The document SU 375298 discloses the use of $CF_2=CFCH_2OH$ in the preparation of O-(2,3,3-trifluoroalkyl) phosphonates.

The document WO 86/07590 relates to pesticides corresponding to the general formula $CF_2=CF—(CH_2)_n—X—R$ in which X can be O, N, S or $CH_2$ and n can have the values from 1 to 4, the value of R depending on the meaning of X.

The use of compounds of formula $CF_2=CF—CH_2Q$ as pesticides is revealed in United States of America Patent U.S. Pat. No. 5,514,717.

W. R. Dolbier et al., in J. Chem. Soc. Perkin Trans., 2, 219–232, 1998, analysed the cyclization activities of hex-5-enyl radicals and disclosed, inter alia, the synthesis of the compound 4,5,5-trifluoropent-4-enol.

T. Dubuffet et al., in J. Organomet. Chem., 341, 11–18, 1998, reveal a process for the opening of oxetanes under the action of fluorinated organolithium derivatives. Test 13 gives access to the compound 4,5,5-trifluoropent-4-enol.

An object of the present invention consists in making available novel fluoromonomers.

This object is achieved by compounds corresponding to the formula I $$CF_2=CF—(CH_2)_m—W \quad (I)$$

in which m has the value 1, 2 or 3,

W represents a $CH(OH)CH_2OH$ group, a

group,

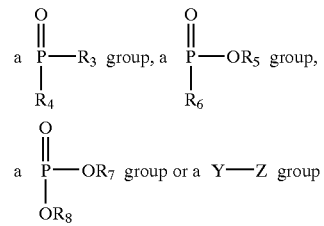

in which $R_1$, $R_2$, $R_3$ and $R_4$ independently represent a hydrogen atom, a $C_1–C_{20}$ alkyl group or an optionally substituted aryl group $R_5$ and $R_6$ independently represent a hydrogen atom, a $C_1–C_{20}$ alkyl group or an optionally substituted aryl group, with the proviso that, when $R_5$ represents a hydrogen atom, $R_6$ is other than a phenyl group when m has the value 1

$R_7$ and $R_8$ independently represent a hydrogen atom, a $C_1–C_{20}$ alkyl group or an optionally substituted aryl group, with the proviso that $R_7$ and $R_8$ do not both represent a hydrogen atom or an ethyl group when m has the value 1

Y represents an oxygen atom or a sulphur atom and

Z represents a hydrogen atom, a $CH_2CH_2OH$ group, a $CH_2COOH$ group or a $COCH_3$ group, with the proviso that, when W represents $CH(OH)CH_2OH$, m has the value 1, when Y represents an oxygen atom, Z is not a hydrogen atom and, when Y represents S, m has the value 3.

More particularly, the present invention provides compounds corresponding to the formula II $$CF_2=CF—C_3H_6—Y—Z \quad (II)$$

in which Y and Z are as defined above.

Another compound according to the present invention corresponds to the formula $$CF_2=CF=CH_2—CH(OH)—CH_2OH.$$

Another object of the present invention is a copolymerization process comprising the reaction of a compound corresponding to the formula I'

$$CF_2=CF—(CH_2)_m—W' \quad (I')$$

in which m has the value 1, 2 or 3,

W' represents a $CH(OH)CH_2OH$ group, a $CH=CH_2$ group,

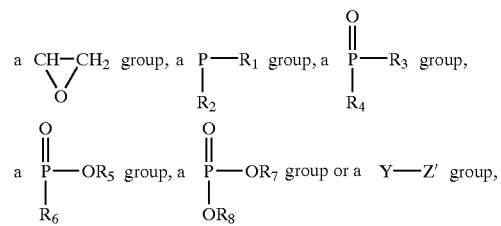

in which $R_1$, $R_2$, $R_3$, $R_4$, $R_5$, $R_6$, $R_7$ and $R_8$ independently represent a hydrogen atom, a $C_1–C_{20}$ alkyl group or an optionally substituted aryl group Y represents an oxygen atom or a sulphur atom and
Z' represents a hydrogen atom, a $CH_2CH_2OH$ group, a $CH_2COOH$ group or a $COCH_3$ group, with a compound corresponding to the formula III

  (III)

in which
X independently represents a hydrogen atom or a fluorine atom
with the proviso that, when m has the value 1 and X represents a hydrogen atom, W' does not represent a

group,
so as to obtain a fluorocopolymer.

One embodiment of the present invention is a copolymerization process comprising the reaction of a compound corresponding to the formula I'
in which
m has the value 1, 2 or 3,
W' represents Y—Z' and Y represents an oxygen atom and Z' represents a hydrogen atom
with a compound corresponding to the formula III in which X independently represents a hydrogen atom or a fluorine atom
so as to obtain a copolymer corresponding to the formula IV

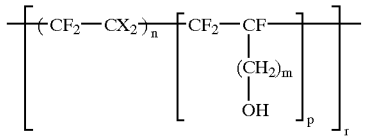  (IV)

n, p and r independently representing natural integers.

An additional aspect of the present invention is a copolymerization process comprising the reaction of a compound corresponding to the formula I'
in which
m has the value 1, 2 or 3,
W' represents Y—Z' and Y represents an oxygen atom and Z' represents a $COCH_3$ group
with a compound corresponding to the formula III in which X independently represents a hydrogen atom or a fluorine atom
so as to obtain a copolymer corresponding to the formula V

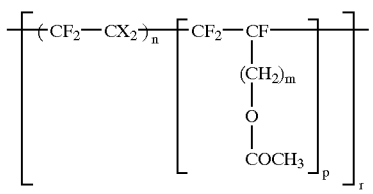  (V)

n, p and r independently representing natural integers.

The present invention also envisages a copolymerization process comprising the reaction of a co compound corresponding to the formula I' in which
m has the value 1, 2 or 3,
W' represents Y—Z' and Y represents a sulphur atom and Z' represents a $COCH_3$ group
with a compound corresponding to the formula III in which X independently represents a hydrogen atom or a fluorine atom
so as to obtain a copolymer corresponding to the formula VI

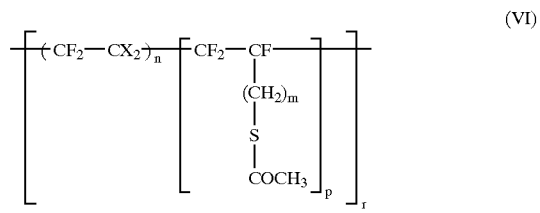  (VI)

n, p and r independently representing natural integers.

According to yet another preferred embodiment, a copolymerization process is provided comprising the reaction of a compound corresponding to the formula I'

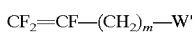  (I')

in which
m has the value 1, 2 or 3,
W' represents a $CH(OH)CH_2OH$ group, a $CH=CH_2$ group,

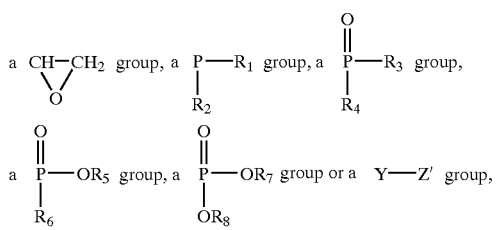

in which
$R_1, R_2, R_3, R_4, R_5, R_6, R_7$ and $R_8$ independently represent a hydrogen atom, a $C_1$–$C_{20}$ alkyl group or an optionally substituted aryl group
Y represents an oxygen atom or a sulphur atom and
Z' represents a hydrogen atom, a $CH_2CH_2OH$ group, a $CH_2COOH$ group or a $COCH_3$ group,
with a compound corresponding to the formula III

  (III)

in which
X independently represents a hydrogen atom or a fluorine atom
and with an olefinic compound
so as to obtain a copolymer.

More particularly, the invention relates to a copolymerization process comprising the reaction of a compound corresponding to the formula I'
in which
m has the value 1, 2 or 3,
W' represents Y—Z' and Y represents an oxygen atom and Z' represents a hydrogen atom
with a compound corresponding to the formula III in which X independently represents a hydrogen atom or a fluorine atom and with an olefinic compound of formula CH$_2$=CHR' with R' representing a hydrogen atom or a C$_1$-C$_4$ alkyl group so as to obtain a copolymer corresponding to the formula VII

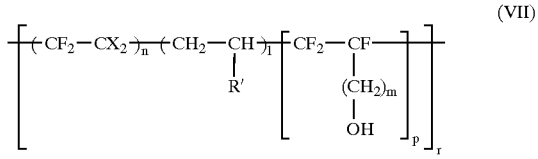

(VII)

l, n, p and r independently representing natural integers. Examples of C$_1$-C$_4$ alkyl groups are ethylene, propylene and butylene.

Fluoropolymers possess outstanding properties, such as their hydro- and bleophobicity, their thermal stability, their chemical inertia to acids, to bases, to solvents and to hydrocarbons, their resistance to ageing and to UV radiation and their low surface tension. They find highly varied applications, often in high-tech industries, such as microelectronics, the chemical industry, the automobile industry, the petroleum industry and the aeronautics industry. However, the high melting and glass transition temperatures of most of these polymers prove to be a limitation on their use which thus requires a significant energy input.

In order to limit this disadvantage, the present invention provides, according to another of its aspects, copolymers corresponding to the general formula VIII

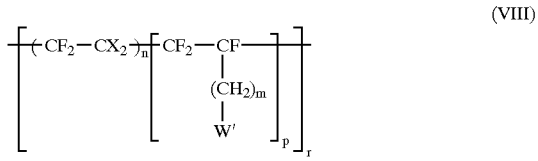

(VIII)

in which
  m has the value 1, 2 or 3,
  X independently represents a hydrogen atom or a fluorine atom,
  n, p and r independently represent natural integers, and
  W' represents a CH(OH)CH$_2$OH group, a CH=CH$_2$ group,

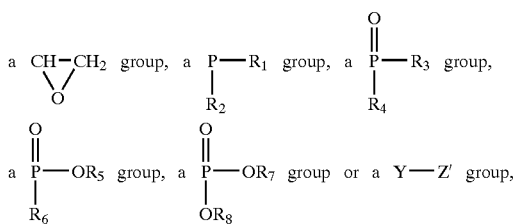

in which
  R$_1$, R$_2$, R$_3$, R$_4$, R$_5$, R$_6$, R$_7$ and R$_8$ independently represent a hydrogen atom, a C$_1$-C$_{20}$ alkyl group or an optionally substituted aryl group
  Y represents an oxygen atom or a sulphur atom and
  Z' represents a hydrogen atom, a CH$_2$CH$_2$OH group, a CH$_2$COOH group or a COCH$_3$ group.

More specifically, the present invention relates to copolymers corresponding to the formula IV

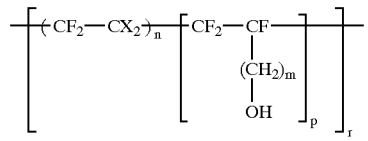

(IV)

in which
  m has the value 1, 2 or 3,
  X independently represents a hydrogen atom or a fluorine atom and
  n, p and r independently represent natural integers.

The present invention also relates to copolymers corresponding to the formula V

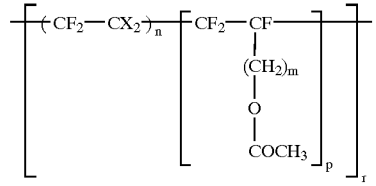

(V)

in which
  m has the value 1, 2 or 3,
  X independently represents a hydrogen atom or a fluorine atom and
  n, p and r independently represent natural integers.

The present invention also relates to copolymers corresponding to the formula VI

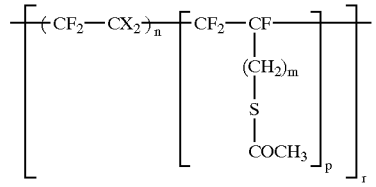

(VI)

in which
  m has the value 1, 2 or 3,
  X independently represents a hydrogen atom or a fluorine atom and
  n, p and r independently represent natural integers.

Other copolymers provided by the present invention are copolymers corresponding to the general formula IX

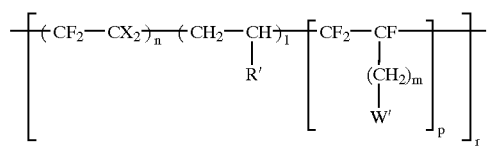

(IX)

in which
  m has the value 1, 2 or 3,
  X independently represents a hydrogen atom or a fluorine atom,
  l, n, p and r independently represent natural integers,
  R' represents a hydrogen atom or a C$_1$-C$_4$ alkyl group and W' represents a CH(OH)CH$_2$OH group, a CH=CH$_2$ group,

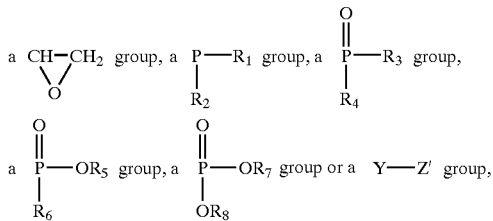

in which

R$_1$, R$_2$, R$_3$, R$_4$, R$_5$, R$_6$, R$_7$ and R$_8$ independently represent a hydrogen atom, a C$_1$–C$_{20}$ alkyl group or an optionally substituted aryl group Y represents an oxygen atom or a sulphur atom and Z' represents a hydrogen atom, a CH$_2$CH$_2$OH group, a CH$_2$COOH group or a COCH$_3$ group.

More specifically, the present invention provides copolymers corresponding to the formula IX, in which m has the value 1, 2 or 3, X independently represents a hydrogen atom or a fluorine atom, W' represents Y—Z' and Y represents an oxygen atom and Z' represents a hydrogen atom l, n, p and r independently represent natural integers and R' represents a hydrogen atom or a C$_1$–C$_4$ alkyl group.

These copolymers comprise monomers exhibiting the CF$_2$=CF—R"—W' structure, R" denoting a spacer arm of variable length targeted at introducing free volumes and at thus reducing the melting and glass transition temperatures.

In order to further improve the properties (particularly mechanical properties) of these fluoro(co)polymers, it is often desirable to crosslink them but this crosslinking to date has required the use of nucleophilic agents (such as diamines or bisphenols) or of radical systems (triallyl cyanurate radicals) or electron bombardment. Consequently, with the aim of avoiding this additional stage, which constitutes a fairly complex procedure, the present invention provides for the incorporation of crosslinking sites (W' functional group in the above fluoromonomers) directly in the (co)polymers.

An additional object of the present invention is a crosslinking process comprising the stages of a) optional deprotection of the functional groups of copolymers obtained above, b) reaction of the resulting copolymers with an unconjugated C$_5$–C$_8$ diene, so as to obtain crosslinked copolymers.

Examples of unconjugated dienes are 1,4-pentadiene, 1,5-hexadiene, 1,7-octadiene and 1,9-decadiene. The use of 1,5-hexadiene as unconjugated diene is particularly preferred.

Finally, the use is also provided of compounds corresponding to the formula I'

$$CF_2=CF-(CH_2)_mW'  \qquad (I')$$

in which m has the value 1, 2 or 3,

W' represents a CH(OH)CH$_2$OH group, a CH=CH$_2$ group,

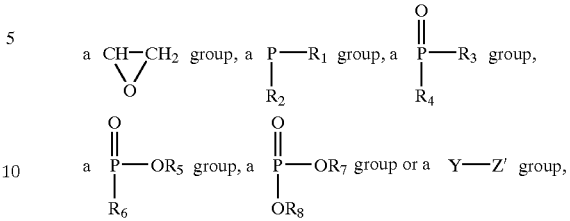

in which

R$_1$, R$_2$, R$_3$, R$_4$, R$_5$, R$_6$, R$_7$ and R$_8$ independently represent a hydrogen atom, a C$_1$–C$_{20}$ alkyl group or an optionally substituted aryl group Y represents an oxygen atom or a sulphur atom and Z' represents a hydrogen atom, a CH$_2$CH$_2$OH group, a CH$_2$COOH group or a COCH$_3$ group, with a compound corresponding to the formula III $$CF_2=CX_2 \qquad (III)$$

in which X independently represents a hydrogen atom or a fluorine atom, preferably a hydrogen atom and optionally with an olefinic compound, to form fluoroelastomers. Examples of olefinic compounds are ethylene, propylene and butylene. The olefinic compound is preferably propylene.

The invention is described in more detail, without implied limitation, in the following examples.

EXAMPLE 1

Preparation of CF$_2$=CFCH$_2$CH(OH)CH$_2$OH a) Radical Addition of Iododichlorotrifluoroethane to Allyl Acetate A mixture composed of 292.2 g (1.050 mol) of iododichlorotrifluoroethane and of 106.5 g (1.065 mol) of allyl acetate was heated with stirring to 55° C. in a three-necked round-bottomed flask equipped with a reflux condenser and a thermometer. 1.4 g (3.5 mmol) of t-butyl cyclohexyl peroxycarbonate were added at this temperature and, after 30 minutes, the addition of an equivalent amount of initiator results in an increase in the temperature of the reaction medium to 70° C. After 30 minutes, an additional 1.4 g of initiator were injected into the mixture and brought about a strong exothermic reaction to 175° C. (over 10 seconds) which rendered the crude product colourless, followed by a dark brown mixture. After evaporating the unreacted iododichlorotrifluoroethane and allyl acetate, the product mixture was distilled. Boiling point=101–105° C./0.2 mmHg (lit. val.: 113° C./2 mmHg or 107–110° C./0.5 mmHg). 236.8 g (0.63 mol) of a dark liquid were obtained (yield=60%).

b) Epoxidation 9.0 g (0.16 mol) of potassium hydroxide were introduced into 40 g of hexane in a three-necked round-bottomed flask equipped with a reflux condenser and a mechanical stirrer. 30.5 g (0.08 mol) of the product resulting from the preceding stage were added dropwise to the mixture at ambient temperature. After completing the addition, the medium was heated to 70° C. with stirring. After cooling, the KI precipitate was removed by filtration and the crude product was distilled. 11.95 g (0.057 mol) of a light brown liquid were obtained, boiling point=53–55° C./23 mmHg (yield=72%).

4,5-Dichloro-4,5,5-trifluoro-1,2-epoxypentane was produced in a proportion of 95.1%, whereas 5,5-dichloro-4,4,5-trifluoro-1,2-epoxypentane was obtained in a proportion of 4.9%.

c) Synthesis of Halogenated 1,2-diol by Opening of the Epoxide Ring

A mixture composed of 5.0 g (23.8 mmol) of 4,5-dichloro-4,5,5-trifluoro-1,2-epoxypentane, 11 ml of demineralized water, 11 ml of dioxane and 4 drops of 12N sulphuric acid was stirred in a single-necked round-bottomed flask equipped with a reflux condenser. The medium was heated at reflux for 12 hours. After the reaction, the dioxane was distilled off and the 4,5-dichloro-4,5,5-trifluoro-1,2-dihydroxypentane was extracted with diethyl ether, dried over sodium sulphate and distilled. Boiling point=28–30° C./26 mmHg. 4.01 g (17.7 mmol) of a colourless liquid were obtained. Yield=75% of 4,5-dichloro-4,5,5-trifluoro-1,2-dihydroxypentane.

d) Dechlorination of the 1,2-diol

A mixture of 2.37 g (0.036 mol) of activated zinc in 25 ml of dry DMF was stirred in a two-necked round-bottomed flask purged with argon and equipped with a reflux condenser. The temperature of the medium was increased to 70° C. and 3.75 g (16.5 mmol) of 4,5-dichloro-4,5,5-trifluoro-1,2-dihydroxypentane obtained above were added dropwise. After reacting for 16 hours, the crude product was cooled to ambient temperature and the unreacted zinc was removed by filtration. The filtrate was treated with 10% HCl and the product was extracted with 1,2,2-trifluorotrichloroethane. After distilling off the solvent, the $CF_2$=$CFCH_2CH(OH)CH_2OH$ was rectified in the form of a colourless liquid (0.88 g, 5.6 mmol, yield=34%), boiling point=106–110° C.

EXAMPLE 2

Preparation of $CF_2$=$CFCH_2CH_2CH_2SCH_2COOH$ a) Photochemical Initiation (Excess of Diene)

A Carius tube comprising 0.055 g (0.3 mmol) of benzophenone, 1.84 g (20 mmol) of thioglycolic acid, 5.00 g (41 mmol) of 1,1,2-trifluoro-1,4-pentadiene and 9.0 g of acetonitrile was cooled in an acetone/liquid nitrogen mixture and degassed under vacuum with 5 freezing/thawing cycles, so as to remove the oxygen. It was subsequently sealed and irradiated under a UV lamp for 16 hours. After the reaction, the tube was frozen in liquid nitrogen and opened, and the solvent and the volatile fractions were evaporated under vacuum (0.01 mmHg). 1,1,2-Trifluoro-6-thiaocten-8-oic acid was distilled first to give 1.9 g of a pale yellow liquid. Boiling point=87–90° C./0.15 mmHg (yield=44%).

b) Photochemical Initiation (Threefold Excess of Thioglycolic Acid)

A similar test to that indicated above was carried out in the presence of 0.083 g (0.46 mmol) of benzophenone, 8.42 g (91.5 mmol) of thioglycolic acid, 3.72 g (30.5 mmol) of 1,1,2-trifluoro-1,4-pentadiene and 10.0 g of acetonitrile. After the same treatment and after the distillation of the excess thioglycolic acid, 5.29 g of a yellow wax were obtained (yield=81%), 3,3,4-trifluoro-2,8-dithianonane-1,9-dioic acid.

c) Radical Initiation in the Presence of Azobisisobutyronitrile (AIBN)

A stirred mixture composed of 0.049 g (0.3 mmol) of AIBN, 1.5 g (16.3 mmol) of thioglycolic acid, 1.99 g (16.3 mmol) of 1,1,2-trifluoro-1,4-pentadiene and 10 g of acetonitrile was heated at 80° C. for 7 hours in a sealed Carius tube. After the reaction and the opening of the tube, the solvent and the unreacted starting materials were evaporated. The brown residue was eluted by flash chromatography on a silica bed with diethyl ether, so as to give an orange oil. The overall yield was 46%. In accordance with the integration of the characteristic signals of the $^1H$ and $^{19}F$ NMR spectra, the yields of 1,1,2-trifluoro-6-thiaocten-8-oic acid, of 3,3,4-trifluoro-2,8-dithianonane-1,9-dioic acid and of 4,5,5-trifluoro-6-thiaoctan-8-oic acid were 26, 37 and 37% respectively.

A similar experiment, initiated by t-butyl cyclohexyl peroxycarbonate, at 60° C. for 5 hours gave 68% of 1,1,2-trifluoro-6-thiaocten-8-oic acid, 7% of 3,3,4-trifluoro-2,8-dithianonane-1,9-dioic acid and 25% of 4,5,5-trifluoro-6-thiaoctan-8-oic acid with an overall yield of 67%.

d) Radical Initiation in the Presence of di-t-butyl Peroxide

Under similar conditions to those described above, 500 g (0.04 mol) of 1,1,2-trifluoro-1,4-pentadiene, 3.80 g (0.04 mol) of thioglycolic acid, 0.117 g (0.8 mmol) of di-t-butyl peroxide and 10 ml of acetonitrile were reacted. After stirring at 140° C. for 6 h and after opening the tube, the solvent was evaporated and the residue was dried at 55° C. under 0.1 mmHg to constant weight. A viscous brown liquid was obtained (4.3 g) which is insoluble in chloroform, acetone, DMF, dimethylacetaminde, THF and 1,2,2-trifluorotrichloroethane. The yield was 49% by mass.

EXAMPLE 3

Preparation of $CF_2$=$CFCH_2CH_2CH_2SCH_2CH_2OH$

The reaction was carried out in a Carius tube comprising a stirred mixture composed of 0.19 g (1.0 mmol) of benzophenone, 2.70 g (34 mmol) of 2-mercaptoethanol, 5.01 g (41 mmol) of 1,1,2-trifluoro-1,4-pentadiene and 9.5 g of acetonitrile. After 6 freezing/thawing cycles, the tube was exposed to UV light at ambient temperature (approximately 25° C.) for 14 hours. After a similar treatment, the crude product was purified and the $CF_2$=$CFCH_2CH_2CH_2SCH_2CH_2OH$ was distilled. 2.03 g of a colourless liquid were obtained (yield=29%); boiling point 65–66° C./1 mmHg, 1,1,2-trifluoro-6-thiaoctanol.

EXAMPLE 4

Preparation of $CF_2CFCH_2OH$ 12.4 g (94 mmol) of 2,2,3,3-tetrafluoropropanol, 62.5 ml (367 mmol) of anhydrous dibutyl ether and 9.5 g (94 mmol) of diisopropylamine were placed in a three-necked round-bottomed flask, dried under vacuum and purged with argon so as to remove moisture, equipped with a reflux condenser, a thermometer and a dropping funnel. The mixture was cooled to approximately 0° C. Subsequently, 100 ml (200 mmol) of a 2M solution of butyllithium in pentane were added dropwise for 30 minutes, so as to prevent the temperature from exceeding 5° C. After stirring for 1 hour, the medium was cooled to −50° C. in an acetone/liquid nitrogen bath. The excess butyllithium was decomposed using a solution of concentrated sulphuric acid (9.4 ml in 30 ml of water) and the mixture was reheated to ambient temperature. The organic phase was separated by successive rinsings with a saturated sodium hydrogencarbonate solution and with water and then dried over anhydrous $MgSO_4$. Subsequently, the products were rectified at atmospheric pressure, so as to separate the pentane (boiling point 35° C.), 32 mmol of 2,3,3-trifluoroallyl alcohol (boiling point 98° C.) and the dibutyl ether (143° C.). Even after a second rectification, dibutyl ether was still present in the fluoroalcohol fraction and the yield obtained by $^1H$ and $^{19}F$ NMR was 34%.

EXAMPLE 5

Preparation of $CF_2\!\!=\!\!CFC_3H_6OH$ a) Radical Addition of 1-iodo-1,2-dichlorotrifluoroethane to Allyl Alcohol 1) Reaction at Atmospheric Pressure A mixture composed of 171.1 g (0.617 mol) of $Cl(C_2F_3Cl)I$ and 98.3 g (1.69 mol) of allyl alchol was stirred in a three-necked round-bottomed flask equipped with a reflux condenser and a thermometer. The mixture was heated to 80° C. and 2.30 g (0.014 mol) of AIBN were added thereto every hour. The reaction was monitored by gas phase chromatography (GC) until the iodinated reactant had been virtually completely consumed. Subsequently, the 2-iodo-4,5,5-trifluoro-4,5-dichloropentanol was distilled. 167.5 g (0.497 mol) of an orange-yellow liquid were obtained. Yield=81%. Boiling point=64–66° C./0.2 mmHg. 2-Iodo-4,5,5-trifluoro-4,5-dichloropentanol.

2) Reaction Carried out in a Carius Tube

A Carius tube saturated with nitrogen was filled with 40.0 g (0.14 mol) of $Cl(C_2F_3Cl)I$, with 17.1 g (0.28 mol) of allyl alcohol and with 0.92 g (0.014 mol) of copper powder. The tube was degassed by 5 freezing/thawing cycles and subsequently sealed. It was introduced into an oven incorporating agitation and heated at 120° C. for 7 h. After the reaction and cooling to ambient temperature, the tube was frozen in liquid nitrogen and subsequently opened. Once ambient temperature was reached, the crude product was diluted in diethyl ether and the copper was removed by filtration. After an acid treatment, neutralization and evaporation of the solvent, the crude product was analysed by GC. The yield was estimated at 62%, 2-iodo-4,5,5-trifluoro-4,5-dichloropentanol.

b) Reduction of 2-iodo-4,5,5-trifluoro-4,5-dichloropentanol 80.0 g (0.27 mol) of tributyltin hydride were added dropwise with stirring to 88.9 g (0.26 mol) of 2-iodo-4,5,5-triflubro-4,5-dichloropentanol placed in a flask, saturated with argon and equipped with a septum, cooled in an ice bath. The addition took 30 minutes, the ice bath having been gradually reduced. The mixture was then stirred for an additional 3 hours at ambient temperature. Subsequently, the reduced derivative, 4,5-dichloro-4,5,5-trifluoropentanol, was distilled under reduced pressure. 47.2 g (0.225 mol) of a light yellow liquid were obtained (yield=86.5%). Boiling point=80–82° C./23 mmHg.

c) Dechlorination of 4,5-dichloro-4,5,5-trifluoropentanol 100 ml of dry DMF were introduced, via a septum, into a three-necked round-bottomed flask rinsed with a flow of argon and equipped with a reflux condenser. 46.8 g (0.72 mol) of zinc activated by 5 cm³ of acetic acid and 5 cm³ of acetic anhydride were introduced, with vigorous stirring, into the flask and the suspension was heated to 90° C. Subsequently, 50.0 g (0.237 mol) of 4,5-dichloro-4,5,5-trifluoropentanol were added dropwise and the temperature was maintained at 90° C. for 4 hours after the completion of the addition. The reaction was monitored by GC, the respective retention times for the trifluorovinyl and chlorinated alcohols being 2.75 and 5.04 minutes respectively. After cooling, the excess zinc was removed by filtration and the crude product was treated with 10% HCl and the fluorinated fraction was extracted with diethyl ether. After distilling off the solvent, the 4,5,5-trifluoropent-4-en-1-ol was rectified. 23.3 g (0.166 mol) of a colourless liquid were obtained. Boiling point=53–55° C./24 mmHg (lit. val.: 95° C./155 mmHg). Yield=70%.

EXAMPLE 6

Preparation of $CF_2\!\!=\!\!CFCH_2CH_2CH_2OCOCH_3$ 31.7 g (0.41 mol) of acetyl chloride were added dropwise to a two-necked round-bottomed flask, cooled in an ice bath, equipped with a reflux condenser (connected to a trap comprising potassium carbonate) and comprising 50.1 g (0.36 mol) of 4,5,5-trifluoro-4-en-1-ol. The reactivity of the two reactants was monitored by sparging of the trap by HCl. After the completion of the addition, the mixture was stirred at ambient temperature until HCl was no longer being evolved (approximately 4 hours). After distillation, 59.3 g (0.326 mol) of 4,5,5-trifluoro-4-pentenyl acetate (colourless liquid) were obtained. Boiling point=56–58° C./21 mmHg. (Yield=91%.).

EXAMPLE 7

Copolymerization of Trifluorovinyl Alcohols with Tetrafluoroethylene (TFE)

a) 2,3,3-Trifluoroallyl Alcohol (FA1)

The copolymerization in solution (in 34% by weight of butyl ether) of TFE with 2,3,3-trifluoroallyl alcohol was carried out by a batchwise process in 30 and 50 cm³ stainless steel autoclaves equipped with a magnetic stirrer, a safety valve, an accurate manometer (±0.01 MPa) and a thermometer (±0.2° C.).

The autoclaves were charged with liquid monomer and initiator (AIBN), subsequently cooled with liquid nitrogen and purged several times by placing under a vacuum and by purging with nitrogen via a stainless steel pipe under a high vacuum. The technique of freezing/thawing cycles was used to remove oxygen from the liquid phase. Subsequently, the desired amount of TFE was condensed in the autoclave.

The polymerization reactions were carried out at various temperatures (60–75° C.) under the pressure suitable for TFE to 10–12% conversion of the monomers.

After the polymerization, the unreacted TFE was purged and the comonomers were first recovered by distillation and subsequently the copolymer was dried under vacuum (10⁻² mmHg at 50–60° C.) to constant weight. The reactivity ratios $r_i$ of the comonomers were calculated by the Tidwell and Mortimer methods and TFE proved to be more reactive than the monomer FA1 ($r_{FA1}$=0.41 and $r_{TFE}$=2.47).

b) 4,5,5-trifluoropent-4-en-1-ol (FA2)

The bulk copolymerization of TFE with 4,5,5-trifluoropent-4-en-1-ol was carried out by a batchwise process in 30 and 50 cm³ stainless steel autoclaves equipped with a magnetic stirrer, a safety valve, an accurate manometer (±0.01 MPa) and a thermometer (±0.2° C.).

The autoclaves were charged with liquid monomer and initiator (AIBN), subsequently cooled with liquid nitrogen and purged several times by placing under a vacuum and by purging with nitrogen via a stainless steel pipe under a high vacuum. The technique of freezing/thawing cycles was used to remove oxygen from the liquid phase. Subsequently, the desired amount of TFE was condensed in the autoclave.

The polymerization reactions were carried out at various temperatures (60–75° C.) under the pressure suitable for TFE to 10–12% conversion of the monomers.

After the polymerization, the unreacted TFE was purged and the comonomers were first recovered by distillation and subsequently the copolymer was dried under vacuum. (10⁻² mmHg at 50–60° C.) to constant weight. The reactivity ratios $r_i$ of the comonomers were calculated by the Tidwell and Mortimer methods and TFE proved to be more reactive than the monomer FA2 ($r_{FA2}$=0.45 and $R_{TFE}$=1.57).

EXAMPLE 8

Emulsion (Ternary) Copolymerization of 4,5,5-trifluoropent-4-en-1-ol with Tetrafluoroethylene (TFE) and Propylene A 250 cm³ stainless steel autoclave (Buchi, Switzerland) was used as container for the terpolymerization of TFE with propylene and 4,5,5-trifluoropent-4-en-1-ol in a batchwise operation. The reactor was equipped with a cooling/heating jacket, with a paddle magnetic stirrer, with a pressure gauge, with a safety valve and with a measuring unit (monitoring of the pressure, stirring and temperature). The components were prepared separately (solutions A and B). The TFE/propylene monomer ratio was maintained at 80/20 mol % (total amount of monomers: 17.7 g) but the initial percentage of 4,5,5-trifluoropent-4-en-1-ol was varied within the range from 1.7 to 14.1 mol %.

The other components of all the compositions were as follows: $H_2O$ (125 g); t-butanol$^a$ (36.8 g/l); $Na_2HPO_4.12H_2O^b$/NaOH$^b$=8/0.8 g/l; $C_7F_{15}COONH_4$(FC-143)$^b$ (10.10 g/l). The redox system comprised (mmol/l): t-butyl peroxobenzoate (TBPB)$^a$ (10.30); $FeSO_4.7H_2O^b$ (0.22); EDTA $2Na.2H_2O^b$ (0.22); $HOCH_2SO_2Na.2H_2O^b$ (12.70), where "a" indicates the components of the solution A and "b" those of the solution B.

The autoclave was closed and the two solutions were purged by a flow of nitrogen. Subsequently, the reactor was charged with the two solutions under an inert atmosphere. The amounts of TFE and of propylene required in order to maintain their initial molar ratio at 80/20 and the initial pressure at 1.55 MPa for each experiment were introduced into the container while stirring at 800–850 rev/min. The temperature of the experiments was maintained by a thermostat at 25±0.2° C. At the end of the copolymerization, the latex was coagulated by cooling the total product mixture with liquid nitrogen and the copolymer isolated was dried under vacuum at 60° C. to constant weight.

EXAMPLE 9

Copolymerization of 4,5,5-trifluoro-4-pentenyl Acetate (FAc) with Vinylidene Fluoride (VDF)

Bulk copolymerization of vinylidene fluoride and of FAc were carried out in Carius tubes made of thick borosilicate in a batchwise process (length: 130 mm, internal diameter: 10 mm, thickness: 2.5 mm, for a total vol of 8 cm$^3$). After having introduced the initiator (0.05 mol % to the mixture of monomers) and the FAc, the tube was connected to a pipe for placing under vacuum and rinsed several times by placing under vacuum and by rinsing with helium. After 5 freezing/thawing cycles, the vinylidene fluoride was trapped under vacuum in the tube, frozen with liquid nitrogen, after the reduction in pressure in a calibrated pressure intermediate metal container. The required amount of vinylidene fluoride (0.50–1.00 g) introduced into the tube was obtained by a relative fall in the pressure in this pressure-reducing container fed initially via a 300 g cylinder of vinylidene fluoride.

The tube, under vacuum and immersed in liquid nitrogen, was sealed and placed in the chamber of an oven incorporating agitation at 120° C. for 17 hours.

After the copolymerization, the tube was frozen in liquid nitrogen and subsequently opened and the total product mixture was dried at 80° C. under 10–2 mmHg to constant weight.

The composition of the copolymer (that is to say the content of vinylidene fluoride and of FAc in the copolymer) was determined by NMR spectroscopy at ambient temperature. The $^1H$ and $^{19}F$ NMR spectra were recorded on Bruker AC-200 or Bruker AC-250 instruments using deuterated acetone or dimethylformamide as solvents and tetramethylsilane (TMS) or CFCl$_3$ as internal references, respectively.

The radical copolymerization of the vinylidene fluoride (VDF) with 4,5,5-trifluoro-4-pentenyl acetate (FAc) was studied over a broad range of initial monomer compositions. $^1H$ NMR spectroscopy and $^{19}F$ NMR spectroscopy made it possible to determine the compositions of copolymers and the two results obtained were in good agreement. The reactivity ratios $r_i$ of the comonomers were calculated by the Tidwell and Mortimer methods and the FAc monomer proved to be more reactive than vinylidene fluoride ($r_{VDF}$=0.17 and $r_{FAc}$=3.22). These values show that a random copolymerization took place. By taking into account the Q and e values of VDF, the Q and e parameters of FAc were calculated: $e_{FAc}$=1.14–1.23 (from $e_{VDF}$=0.40–0.50) and $Q_{FAc}$=0.04–0.06 (in contrast to $Q_{VDF}$=0.008–0.015).

EXAMPLE 10

Copolymerization of 1-thio-4,5,5-trifluoro-4-pentenyl Acetate (FSAc) with Vinylidene Fluoride (VDF)

A 200 ml Hastelloy autoclave, equipped with a valve, a manometer and a safety disc and provided with a magnetic stirrer, was charged with 0.2507 g (1.72 mmol) of t-butyl peroxide, with 4.01 g (0.0202 mol) of FSAc and with 70 g of acetonitrile. After being closed, the autoclave was placed in a bath of liquid nitrogen/acetone; subsequently, it was placed under vacuum and purged with gaseous nitrogen, so as to remove the oxygen. 20.25 g (0.316 mol) of vinylidene fluoride were then introduced. After reheating to ambient temperature, the autoclave was introduced into an oil bath with the following heating cycle: 5 h at 120° C., 2 h at 130° C. and subsequently 6 h at 140° C. After the reaction, the container was placed in an ice bath and the unreacted vinylidene fluoride was released.

A portion of the acetone of the reaction mixture was evaporated and the vinylidene fluoride/FSAc copolymer was precipitated from a threefold excess of heptane. The solid polymer was dried at 60–70° C. under vacuum to constant weight.

4.36 g of a white solid were obtained (yield of approximately 18%).

This powder was soluble in acetone, acetonitrile, DMF and THF at ambient temperature but it was insoluble in cyclohexane, hexane, heptane and toluene, even on heating slightly (40° C.).

EXAMPLE 11

Crosslinking of Poly(vinylidene Fluoride) (PVDF) Carrying Mercapto Functional Side Groups a) Hydrolysis of the VDF/FSAc Copolymer 10 ml of methanol and 10 ml of acetone were introduced into a three-necked round-bottomed flask equipped with a reflux condenser and an inlet for a flow of nitrogen. After degassing and after sparging this mixture with nitrogen, 0.18 g (2.77 mmol) of potassium cyanide and 3.2 g (approximately 1.28 mmol) of VDF/FSAc copolymer were added.

The mixture was stirred at ambient temperature for 15 h. After the reaction, the hydrolysedcopolymer was precipitated from water. 1.79 g of PVDF carrying mercapto functional side groups were obtained.

b) Crosslinking Proper

A small tube made of borosilicate comprising 1.13 g (0.45 mmol) of PVDF carrying mercapto functional side groups, 1.30 g (15.8 mmol) of 1,5-hexadiene, 0.055 g (0.31 mmol) of t-butyl peroxypivalate and 5.04 g of acetonitrile was degassed and purged with helium. Subsequently, after 5 freezing/thawing cycles, it was sealed under vacuum and introduced into an oven with stirring. The tube was stirred for 5 h at 75° C. After the reaction, a beige precipitate appeared at the bottom of the tube. After freezing in liquid nitrogen, the tube was opened. The solvent and the excess 1,5-hexadiene were evaporated and the brown solid was dried at 70° C. under vacuum for 3 h (1.43 g were obtained). The product was insoluble in polar and nonpolar solvents.

What is claimed is:

1. A copolymer corresponding to the formula VIII

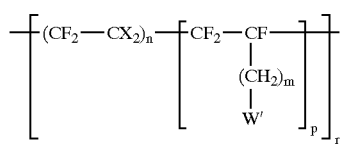

(VIII)

in which m has the value 1, 2 or 3,

X independently is selected from the group consisting of a hydrogen atom and a fluorine atom, n, p and r independently represent natural integers, and W' is selected from the group consisting of a CH(OH) CH$_2$OH group, a CH=CH$_2$ group,

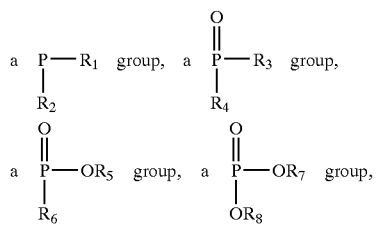

in which $R_1$, $R_2$, $R_3$, $R_4$, $R_5$, $R_6$, $R_7$ and $R_8$ independently are selected from the group consisting of a hydrogen atom, a $C_1$–$C_{20}$ alkyl group and an optionally substituted aryl group and a Y—Z group chosen from (1) a Y—Z group in which Y represents an oxygen atom and Z is selected from the group consisting of a CH$_2$CH$_2$OH group, a CH$_2$COOH group and a COCH$_3$ group, (2) a Y—Z group in which Y represents a sulphur atom and Z is selected from the group consisting of a hydrogen atom, a CH$_2$CH$_2$OH group, a CH$_2$COOH group and a COCH$_3$ group.

2. The copolymer according to claim 1, in which Y represents an oxygen atom and Z represents a COCH$_3$ group.

3. The copolymer according to claim 1, in which Y represents a sulphur atom and Z represents a COCH$_3$ group.

4. A copolymer corresponding to the formula IX

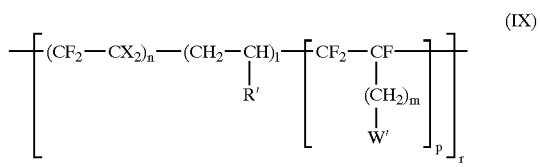

(IX)

in which m has the value 1, 2 or 3,

X independently is selected from the group consisting of a hydrogen atom and a fluorine atom, l, n, p and r independently represent natural integers, R' is selected from the group consisting of a hydrogen atom and a $C_1$–$C_4$ alkyl group and W' is selected from the group consisting of a CH(OH) CH$_2$OH group, a CH=CH$_2$ group,

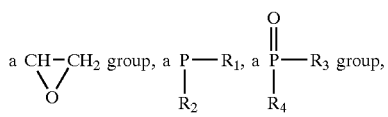

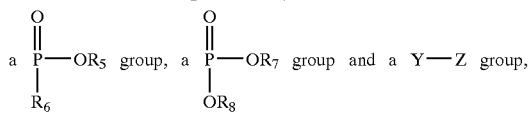

in which $R_1$, $R_2$, $R_3$, $R_4$, $R_5$, $R_6$, $R_7$ and $R_8$ independently are selected from the group consisting of a hydrogen atom, a $C_1$–$C_{20}$ alkyl group and an optionally substituted aryl group, Y is selected from the group consisting of an oxygen atom and a sulphur atom and Z is selected from the group consisting of a hydrogen atom, a CH$_2$CH$_2$OH group, a CH$_2$COOH group and a COCH$_3$ group.

5. A crosslinking process comprising the stages of a) optional deprotection of the functional groups of copolymers according to claim 4, b) reaction of the resulting copolymers with an unconjugated $C_5$–$C_8$ diene, so as to obtain crosslinked copolymers.

6. The crosslinking process according to claim 5, wherein said unconjugated diene is 1,5-hexadiene.

* * * * *